United States Patent [19]

Nagasawa et al.

[11] Patent Number: 4,520,100

[45] Date of Patent: May 28, 1985

[54] METHOD FOR MEASURING THROMBIN

[75] Inventors: Takeshi Nagasawa; Katsumasa Kuroiwa; Katsuyuki Takabayashi, all of Koriyama, Japan

[73] Assignee: Nitto Boseki Co. Ltd., Fukushima, Japan

[21] Appl. No.: 578,805

[22] Filed: Feb. 10, 1984

Related U.S. Application Data

[62] Division of Ser. No. 406,025, Aug. 6, 1982, Pat. No. 4,450,105.

[30] Foreign Application Priority Data

Sep. 28, 1981 [JP] Japan ................. 56-153472

[51] Int. Cl.³ .................. C12Q 1/56; C12Q 1/38
[52] U.S. Cl. ............................ 435/13; 435/23
[58] Field of Search ................ 435/4, 13, 23, 24

[56] References Cited

U.S. PATENT DOCUMENTS 4,169,015 9/1979 Ekenstam et al. ............... 435/13
4,275,153 6/1981 Gargiulo et al. ............... 435/13

FOREIGN PATENT DOCUMENTS 55-15702 2/1980 Japan ................. 435/24

Primary Examiner—Esther M. Kepplinger
Attorney, Agent, or Firm—Bert J. Lewen

[57] ABSTRACT

A novel substrate for measuring thrombin which has chromophoric and fluorescent properties on thrombin or a thrombin-like enzymes and is represented by a compound of the following general formula or a salt thereof:

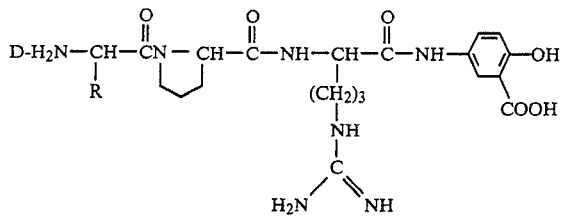

wherein R represents

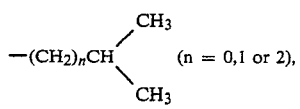

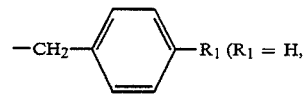

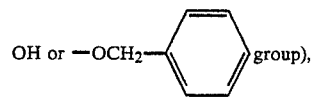

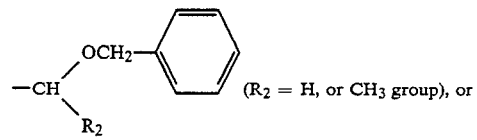

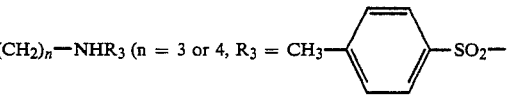

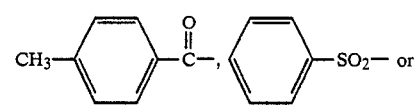

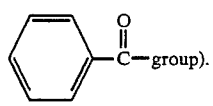

1 Claim, No Drawings

METHOD FOR MEASURING THROMBIN

This is a division of application Ser. No. 406,025, filed Aug. 6, 1982, U.S. Pat. No. 4,450,105.

The present invention relates to novel chromophoric and fluorescent substrates for thrombin and thrombin-like enzymes. The substrates of the present invention, as compared with the heretofore reported substrates, can quantitatively analyze thrombin with extremely good selectivity and are especially suitable for researches on reaction in which thrombin is formed, inhibited or consumed, or measurements of factors relating thereto, for example, measurements of prothrombin, antithrombin III and heparin.

The introduction of synthetic substrates in coagulation and linear dissolution reactions was started with the employment of arginine esters such as TAMe (Tos-Arg-OMe) etc. synthesized by S. Sherry et al in 1954 [J.S.C., 208, 95–105 (1954)] in the measurement of the esterase activity of thrombin as the substrate, but there have been problems such as low specificity and sensitivity of the substrate since the ester melting activity did not correspond to the coagulation activity. However, thanks to the recent progress of peptide chemistry, a peptide substrate, Bz-Phe-Val-Arg-PNA (S-2160) resembling the amino acid structure of the part of fibrinogen cleaved by thrombin was synthesized by Blömback et al [Thromb. Research 1 267–278 (1972)], and this has gradually become to be used in researches and testings, because the enzymatic chemical spectroscopy based on the yellow color development of paranitroaniline (PAN) which has been liberated by having undergone the enzymatic reaction is easy, the preparation of the reagents is easy and so forth. Further, as substrate for thrombin, Tos-Gly-Pro-Arg-PNA (trade name: CHR-TH, Pentapharm Co.) [Japanese Patent Application Laid-open No. 52-3494] H-D-Phe-Pip-Arg-PNA (S-2238, Kabi Co.) [Japanese Patent Application Laid-open No. 52-24590] have been successively developed, and thereafter a fluorescent peptide substrate to which aminomethylcoumarin (AMS) similarly emitting fluorescence when liberated had been attached was also developed by Iwanaga et al (1977) [J. Biochem., 82 1495–1498 (1977)].

On the other hand, it is important for the synthetic substrates for measuring enzymes to satisfy four points, namely, high sensitivity and specificity for the enzyme, good solubility in aqueous or biological testing solutions and easy detectability of the decomposition product.

Among the above, the high specificity for the enzyme to be measured is of a particular importance.

In general, when prothrombin, antithrombin III or the like in the plasma is to be measured utilizing a chromophoric substrate, if it undergoes a cross reaction with plasmin, FXa, urokinase etc. which are coagulation and linear dissolution related enzymes other than thrombin and are presumably present in the plasma, accurate measurement can not be expected.

In addition, where prothrombin (F-II) is to be measured, generally as the most suitable method, thrombin (sic) is converted to thrombin with FXa or thromboplastin in the presence of phospholipids, Ca++ and factor V and acted on a substrate for thrombin, and the activity is measured, but in this case, it is essential that the FXa present in the reaction system does not react with the substrate.

As the best substrates for thrombin ever developed, the above-described CHR-TH and S-2238 may be mentioned, but they are not entirely satisfactory from the view of their substrate specificity.

In other words, for instance, CHR-TH considerably reacts with plasmin, Factor Xa, urokinase (UK) etc. in addition to thrombin among the coagulation and linear dissolution related enzymes and also it is known that even S-2238 which is said to be of relatively good selectivity, considerably reacts with plasmin or UK.

Further, as with the above-described both substrates, the method for colorimetrically analyzing the yellow color of the produced nitroaniline can not get rid of the influence of the plasma components.

The present inventors have been endeavoring to develop and research novel substrates for thrombin in order to improve the above points, and have discovered substrates having excellent properties, which have remarkably improved the above-described disadvantages and satisfied the above-described four requisites.

In other words, by employing 3-carboxy-4-hydroxyanilide (abbreviation: CHA) instead of the chromophoric group p-nitroanilide (abbreviation: pNA) heretofore developed and used for the substrates, we have now successfully developed the desired substrates for thrombin having remarkably improved selectivity as compared with the conventional substrates, by inhibiting reactivity with enzymes other than thrombin, e.g. enzymes such as plasmin, FXa etc.

The novel chromophoric and fluorescent substrates by the present invention are represented by the following general formula:

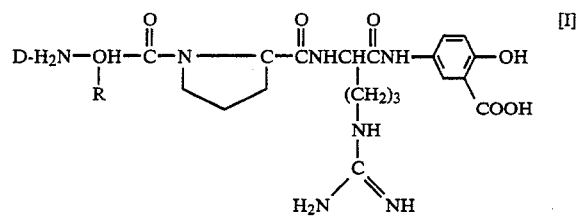

wherein R represents

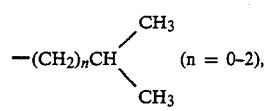   $(n = 0-2)$,

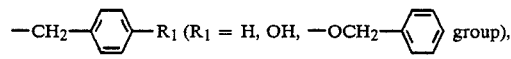

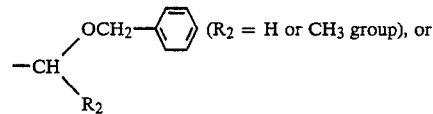

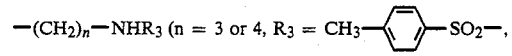

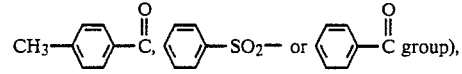

and are characterized by utilizing 3-carboxy-4-hydroxyanilide as the chromophoric group. Since the present substrates have extremely hydrophilic groups such as the hydroxyl group and carboxyl group in the chromophoric group, they have superior solubility in water. Representative applications of the substrates [I] of the present invention reside in using the substrates for measuring thrombin. That is to say, a substrate of the present invention is reacted with thrombin to form 3-carboxy-4-hydroxyaniline, the aniline is oxidatively condensed to form a colored compound, and the compound is quantitatively analyzed either by colorimetry, or by fluorometry at 328 nm in the exceted state or at 540 nm using fluorescence, thereby the thrombin activity is specifically measured.

The feature of the present invention resides in their excellent substrate specificity for thrombin as described above. Relative activity of the novel substrate, for example, H-D-Phe-Pro-Arg-CHA as well as those of S-2238, CHR-TH and H-D-Phe-Pro-Arg-PNA containing PNA as the chromophic group and having the amino acid arrangement same as that of the above novel substrate which is prepared for reference towards the various coagulation and linear dissolution related enzymes such as thrombin (TH), plasmin (PL), kallikrein (KL), Factor Xa(FXa), urokinase (UK) are shown in Table 1 where the activity of the H-D-Phe-Pro-Arg-PAN is set as 100. From the Table, it can be seen that the reactivity with plasmin, FXa, UK etc., in the case of the CHA based novel substrate, is as remarkably low as only 1% of plasmin, 9% of FXa and 2% of UK have reacted, and thus the selectivity has been remarkably improved as compared with 225% and 64% of plasmin, 1165% and 42% of FXa and 300% and 74% of UK in the cases of the CHR-TH and S-2238 respectively.

These facts indicate that the compounds of the present invention are extremely superior as the substrates for thrombin.

xylenol, thymol, o-cresol, o-ethylphenol etc. in the alkaline side.

Further, as the oxidant for the oxidative condensation, while various agents such as hydrogen peroxide, persulfuric acid salts etc. are employed, metaperiodic acid is suitable.

The dye produced by the oxidative condensation of 3-carboxy-4-hydroxyaniline and the above-described coupler has a maximum absorption wavelength widely distributed between 560–770 nm depending on the coupler but its fluctuation in color development with temperatures is very small and hence stable, thus this method is suitable for the measurement of the thrombin activity.

Furthermore, when the chromophoric sensitivities are compared, in the case of p-nitroaniline, absorbance is 10,600 at 405 nm which is a wavelength employed for general measurements, whereas in the color development using o-ethylphenol and 3-carboxy-4-hydroxyaniline, absorbance is 29,000 at $\lambda=645$ nm and in the color development using 2.6-xylenol and 3-carboxy-4-hydroxyaniline absorbance is 21,600 at $\lambda=615$ nm; thus absorbance in the color development using 3-carboxy-4-hydroxyaniline is large and extremely advantageous in measurement.

Since the substrates of the present invention have hydrophilic functional groups and the solubility in water is very good, and hence do not particularly need dissolving aids, such as surfactants, organic solvents, etc., they have advantages that they are very easily controlled in the reagent preparation or measuring operation and that the substrate concentration just necessary and satisfactory for the reaction can be employed.

Furthermore, one of the features of the present invention is that the measurement is hardly influenced by the extraneous matters in a vital sample. This is because,

TABLE 1

| Relative Activity to Various Enzymes | | | | | |
|---|---|---|---|---|---|
| | TH | PL | KL | FXa | UK |
| S-2238 H—D-Phe—Pip—Arg—PNA | 9.3 (0.255) | 64 (0.139) | (0.008) | 42 (0.023) | 74 (0.014) |
| CHR—TH ToS—Gly—Pro—Arg—PNA | 116 (0.318) | 225 (0.489) | (0.020) | 1165 (0.641) | 300 (0.057) |
| TH—PNA H—D-Phe—Pro—Arg—PNA | 100 (0.274) | 100 (0.217) | (0.007) | 100 (0.055) | 100 (0.019) |
| (Substrate of the NT—C Invention) H—D-Phe—Pro—Arg—CHA | 55 (0.451) | 1 (0.009) | (0.007) | 9 (0.014) | 2 (0.001) |

Initial Substrate Concentration So = 0.54 mM.
The numerals in brackets are the measured O.D. values.

The applications of the compounds of the present invention are, as already described, as the substrates for measuring the thrombin activity. In this case, the thrombin activity is measured by reacting a substrate of the present invention with thrombin in a buffer solution having a pH of 8.0 to 8.7 to form 3-carboxy-4-hydroxyaniline, oxidatively condensing the aniline with an appropriate coupler to convent to a colored substance, and quantitatively analyzing the substance either by colorimetry or by fluorometry at 328 nm in the excited state or at 540 nm using fluorescence.

As the coupler, there may be employed anilinic compounds such as N,N-diethylaniline when the color is developed in the acidic side, and phenolic and naphtholic compounds such as 2,5-xylenol, 2,6-xylenol, 2,3- although the measurement is made at a wavelength of 560 nm or less in the case of p-nitroaniline compounds, the measurement is made at a wavelength of 560 nm or higher in the present invention, and therefore there is no such influence by the extraneous matters in the sample, and further also since the reducing substances (uric acid and ascorbic acid) in the sample are decomposed by the excess oxidizing agent, the accurate measuring results are obtained, also owing to the high specificity inherent to the substrate.

As described above, it is evident that the compounds of the present invention are very excellent as the substrates for measuring the thrombin activity as compared with the conventional products.

The compounds of the formula [I] of the present invention are synthesized by a process well known in peptide chemistry such as a process described in "Methoden der Organischen Chemie" (von Eugen Müller, Band XV/1, XV/2, Synthese von Peptiden, 1974, Georg Thieme Verlag Stuttgart).

As the α-amino protecting group, it is advantageous to employ a carbobenzoxy or t-butyloxycarbonyl or related group, e.g. p-methoxy-p-nitro- or p-methoxyphenylazolcarbobenzoxy etc.

For protecting the δ-guanidyl group in the arginyl group, it is advantageous to employ protonization, or a carbobenzoxy group (δ,δ-diprotection). The coupling of the two amino acids or the coupling of the dipeptide and the amino acid may be effected by the activation of the α-carboxyl group. For instance, the activated form may be N-hydroxysuccinimide, p-nitrophenol, trichlorophenol, 4,6-dimethylpyrimidyl-2-thio, etc. The activation of the above-described ester derivative is advantageously conducted in the presence of a carbodimide, for example, N,N-dicyclohexylcarbodiimide (DCC).

The substrate synthesis may be effected by attaching the chromophoric group to the arginyl group and successively carrying out the couplings, or it is possible to synthesize the N-terminated dipeptide fragment itself and then attach it to the arginyl group having the chromophoric group.

The present invention is now described in more detail by the following examples, but the present invention should in no way be restricted to these examples.

| [1]Abbreviations | |
|---|---|
| Arg = Arginine | DMF = Dimethylformamide |
| Leu = Leucine | MeOH = Methanol |
| Lys = Lysine | THF = Tetrahydrofuran |
| Phe = Phneylalanine | NEM = N—Ethylmorpholine |
| Pro = Proline | ESA = Ethanesulfonic acid |
| Thr = Threonine | TEA = Triethylamine |
| Tyr = Tyrosine | TFA = Trifluoroacetic acid |
| Val = Valine | DCC = Dicyclohexylcarbodiimide |
| Z = Benzyloxycarbonyl | —CHA = 3-Carboxy-4- |
| Boc = t-Butyloxycarbonyl | hydroxyanilide |
| Z(OMe) = p-Methoxy- | —SDP = 4,6-Dimethyl- |
| benzyloxycarbonyl | pyrimidine-2-thio |
| Tos = p-Tolylsulfonyl | Bzl = Benzyl |
| AcOH = Acetic acid | TLC = Thin layer chromatography |
| AcOEt = Ethyl acetate | GPC = Gel permeation chromatography |

(Note: Unless otherwise specified, the amino acids are in the L-form.)

[2] Thin layer chromatography

For TLC analyses, silica gel $F_{254}$ (manufactured by Merck Co.) Plates were employed, and the developing solvents were as follows:
Rf$_1$; CHCl$_3$:MeOH:AcOH:H$_2$O = 80:20:2.5:5
Rf$_2$; n-BuOH:AcOH:H$_2$O = 4:1:1
Rf$_3$; n-BuOH:AcOH:H$_2$O = 4:1:2
Rf$_4$; n-BuOH:AcOH:H$_2$O = 4:1:5

[3] For Gel permeation, hydroxypropylated cross-linked dextran gel Sephadex L-H-20 (trade name) manufactured by Pharmacia Fine Chemical Co. (Sweden) was employed.

EXAMPLE 1

Synthesis of H-D-Phe-Pro-Arg-CHA

I. Z(OMe)-Arg(Z$_2$)-CHA 60.6 g (0.1 mole) of Z(OMe)-Arg(Z$_2$)-OH and 15.4 g (0.1 mole) of HSDP

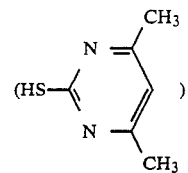

were dissolved in 500 ml of THF, to which was added dropwise to a solution of 20.6 g (0.1 mole) of DCC in 250 ml of THF at 0°–5° C. and the reaction was effected. After reacting at room temperature (20°–25° C.) for 18 hours, the precipitated dicyclohexylurea (DCHU) was filtered off, and the THF was distilled off under reduced pressure, to obtain 54 g (74%) of the synthesized oily crude active ester, PMZ-Arg(Z$_2$)-SDP, which was directly used in the subsequent reaction.

54 g (0.4 mole) of the active ester PMZ-Arg (Z$_2$)-SDP synthesized above was dissolved in 150 ml of THF, which was then added dropwise to a solution of 11.4 g (0.74 mole) of 5-aminosalicyl acid and 20.8 ml (0.148 mole) of TEA in 80 ml of DMF at 0°–5° C. and the reaction was effected. Further reacting at room temperature for 18 hours, the solvent was distilled off, the residue was dissolved in 800 ml of AcOEt, washed with 400 ml of 5% cold aqueous HCl twice, and the precipitated crystals were filtered out and dried, to obtain 36.8 g (67.6%) of Z(OMe)-Arg(Z$_2$)-CHA.

RF$_1$=0.52, m.p. 182°–185° C., [α]$_D$+11.0 (Cl. DMF)

II. BOC-Pro-Arg(Z$_2$)-CHA

To 37.1 g (0.05 mole) of Z(OMe)-Arg(Z$_2$)-CHA were added 15 ml of anisole and 250 ml of TFA, and the reaction was effected at room temperature for 2 hours. After completion of the reaction, the TFA was distilled off under reduced pressure, and the residue was then treated with dry ether to crystallize, thereby 26.3 g (76%) of TFA-H-Arg(Z$_2$)-CHA was obtained.

[α]$_D$+22.4 (Cl. DMF) 17.5 g (0.0255 mole) of the TFA.H-Arg(Z$_2$)-CHA was dissolved in 102 ml of 0.75 N NEM/DMF, and a solution of 8.6 g (0.0255 mole) of BOC-Pro-SDP in 15 ml of DMF was added dropwise thereto at 0°–5° C., followed by the reaction. After reacting at room temperature (20°–25° C.) for 18 hours, the DMF was distilled off under reduced pressure, the residue was dissolved in 750 ml of AcOEt, and washed with 250 ml of cold 5% HCl four times and then with 250 ml of saturated aq. NaCl twice. After drying on MgSO$_4$, the solvent was distilled off under reduced pressure, to obtain crude BOC-Pro-Arg(Z$_2$)-CHA as a foam, which was recrystallized from IPA/IPE to obtain 7.4 g (37.3%) of II.

Rf$_1$=0.53, m.p. 110°–135° C., [α]$_D$–18.0 (Cl.DMF)

III. Z-D-Phe-Pro-Arg(Z$_2$)-CHA 12.7 g (0.016 mole) of the BOC-Pro-Arg(Z$_2$)-CHA was treated in 41 ml of 2N HCl/AcOH at room temperature for 2 hours, to remove the BOC group, and the reaction mixture was submerged in ether. The precipitate was filtered out and dried to obtain 12.4 g (98.4%) of HCl.H-Pro-Arg(Z$_2$)-CHA.

Rf$_1$=0.60, m.p. 184°–187° C., [α]$_D$–25.8 (Cl. MeOH)
7.43 g (10.5 mmole) of the HCl.H-Pro-Arg(Z$_2$)-CHA and 4.5 ml (31.5 mmole) of TEA were dissolved in 66 ml of DMF, to which was added dropwise, with ice-cooling to −5° C. to 0° C., a solution of 4.5 g (10.5 mmole) of Z-D-Phe-SDP in 33 ml of DMF, followed by the reaction. After 2 hours, the temperature was allowed to warm to room temperature, and the reaction was effected at normal temperature for 15 hours, after which the DMF was distilled off, the residual oily matter was dissolved in 60 ml of MeOH, submerged in 3000 ml of 3% aqueous citric acid solution, and the precipitated crystals were filtered out and dried, to obtain 7.8 g of crystals. They were gel permeated through Sephadex LH-20 using MeOH as the developing solvent to obtain 3.8 g of crystals.

$Rf_1=0.55$, m.p. 224°–228° C., $[\alpha]_D-40.2$ (Cl. MeOH)
Elementary analysis for $C_{51}H_{53}N_7O_{12}.1.5H_2O$

|  | C | H | N |
|---|---|---|---|
| Found: | 62.46 | 5.70 | 10.17 |
| Calc'd: | 62.31 | 5.74 | 9.97 |

IV. 2HCl.H-D-Phe-Pro-Arg-CHA 2.9 g (3.03 mmole) of the Z-D-Phe-Pro-Arg($Z_2$)-CHA was dissolved in 130 ml of MeOH, 5 or 6 drops of AcOH was added, and the catalytic reduction was effected using 1 g of palladium black as the catalyst. After the reaction, the MeOH solution was concentrated, the residue was dissolved in 5 ml of 2N HCl/AcOH and added to 200 ml of ether to submerge. The precipitated crystals were filtered out, and dried on KOH, to obtain 1.30 g (68%) of 2HCl.H-D-Phe-Pro-Arg-CHA.

m.p. 213° C. (dec.), $[\alpha]_D-109.2$ (C 0.5, MeOH)
Elementary analysis for $C_{27}H_{35}N_7O_6.AcOH.3/2-H_2O.2HCl$

|  | C | H | N |
|---|---|---|---|
| Found: | 48.61 | 6.04 | 14.05 |
| Calc'd: | 48.81 | 6.21 | 13.78 |

EXAMPLE 2

2HCl.H-D-Thr-(OBzl)-Pro-Arg-CHA

V. BOC-Pro-Arg-CHA, $C_{23}H_{34}O_7N_6$, 506.563

6.4 g (8.3 mmole) of the BOC-Pro-Arg($Z_2$)-CHA was dissolved in 120 ml of MeOH, and reduced with hydrogen in the presence of palladium black for 6 hours. After the reaction, the catalyst was filtered off, the MeOH was distilled off under reduced pressure, the residue was treated with ether to crystallize, the crystals were filtered out and dried, to obtain 3.6 g (85.7%) of BOC-Pro-Arg-CHA.

$Rf_2=0.48$, m.p. 199°–203° C., $[\alpha]_D-76.0$ (Cl.MeOH), 2HCl.H-Pro-Arg-CHA, $C_{18}H_{26}O_5N_6.2HCl$, 479.367

3.0 g (5.9 mmole) of the BOC-Pro-Arg-CHA was treated in 29.5 ml (59 mmole) of 2N HCl/AcOH at room temperature for 2 hours, and poured into ether. The precipitate was filtered out and dried, to obtain 2.8 g (100%) of 2HCl.H-Pro-Arg-CHA.

$Rf_4=0.11$, m.p. 203° C. (dec.), $[\alpha]_D-42.4$ (Cl. MeOH)

VI. BOC-D-Thr(OBzl)-Pro-Arg-CHA, $C_{34}H_{46}N_7O_9$, 696.788

0.959 g (2.0 mmole) of the 2HCl.H-Pro-Arg-CHA was dissolved in 8 ml of 0.75 N NEM/DMF, to which was added 0.863 g (2.0 mmole) of BOC-D-Thr(OBzl)-SDP at 0°–5° C., and the reaction was effected at room temperature for 18 hours, after which the reaction mixture was poured into 2000 ml of cold 1/1 solution of 10% citric acid/sat. aqueous Nacl. The precipitate was filtered out and dried, to obtain 1.07 g (72.7%) of BOC-D-Thr(OBzl)-Pro-Arg-CHA.

$Rf_2=0.61$, m.p. 180°–195° C.

VII. 2HCl.H-D-Thr(OBzl)-Pro-Arg-CHA, $C_{29}H_{41}N_7O_7Cl_2$, 670.599

0.9 g (1.2 mmole) of the BOC-D-Thr(OBzl)-Pro-Arg-CHA was treated with 10 ml (20 mmole) of 2N HCl/AcOH at room temperature for 2 hours, and the reaction mixture was poured into ether. The precipitate was filtered out and dried, to obtain crude 2HCl.H-D-Thr(OBzl)-Pro-Arg-CHA, which was then gel permeated through Sephadex LH-20 (4×112 cm) column using MeOH as the developing solvent, to obtain 0.32 g (40.2%).

$Rf_2=0.33$, m.p. 183°–190° C.

EXAMPLE 3

By similar procedures, the substrates given below were synthesized.

| Substrates of the Invention | m.p. | Rf |
|---|---|---|
| 1 NT-A  H—D-Val—Pro—Arg—CHA.2HCl | 219° C. (dec.) | $Rf_2 = 0.09$ |
| 2 NT-B  H—D-Leu—Pro—Arg—CHA.2HCl | 189° C. (dec.) | $Rf_2 = 0.22$ |
| 3 NT-D  H—D-Ser(OBzl)—Pro—Arg—CHA.2HCl | 165–167° C. | $Rf_3 = 0.50$ |
| 4 NT-F  H—D-Tyr(OBzl)—Pro—Arg—CHA.2HCl | 198° C. (dec.) | $Rf_3 = 0.38$ |
| 5 NT-G  H—D-Lys(ToS)—Pro—Arg—CHA.2MSA | 175–176° C. | $Rf_2 = 0.28$ |

EXAMPLE 4

The specificities of the newly synthesized substrates were tested by reacting them with various enzymes respectively.

TESTING METHOD (1) Substrate solution concentration: 3.5 mmole/liter $H_2O$ (2) Buffer: Tris-hydrochloric acid buffer 50 mmole/l NaCl 150 mmole/l (0.875%)
was employed, and the PH for the reaction was as follows depending on the enzyme.

| Enzyme | pH (25° C.) |
|---|---|
| Thrombin (TH) | 8.4 |
| Plasmin (PL) | 7.4 |
| Kallikrein (KL) | 7.9 |
| Factor-Xa (FXa) | 8.4 |
| Urokinase (UK) | 8.2 |

(3) Enzymes used

|  | Origin | Manufacturer | Lot No. | Units |
|---|---|---|---|---|
| Thrombin | Cow | Mochida* (Japan) | OA 411 | 1.0 NIH/ml |
| Plasmin | Pig | Sigma (U.S.A) | 118c-02841 | 0.032 |

-continued

| | Origin | Manufacturer | Lot No. | Units |
|---|---|---|---|---|
| Kallikrein | Pig | Sigma (U.S.A) | 118C-0214 | CU/ml 1.0 BAEE-U/ml |
| F-Xa | Cow | Sigma (U.S.A) | 60 F-3953 | 0.4 U/ml |
| Urokinase | Human | Mochida* (Japan) | A-131 | 1000 IU/ml |

*Mochida Pharmaceutical Co., Ltd.

(4) Reaction terminating solution (PNA): 10% Acetic acid (5) Color developing reagent (CHA) o-Ethylphenol 7.0 mmole+NaIO$_4$ 1.5 mmole/0.2 N-KOH

MEASURING METHOD 0.5 ml of the buffer solution and 0.05 ml of the enzyme reagent were taken into a silicon-treated hard glass test tube or a plastic test tube, and preheated in a constant temperature bath at 37° C. for 5 minutes. Thereafter, 0.1 ml of the substrate solution was added to effect the enzymatic reaction at 37° C. for 10 minutes. Exactly after 10 minutes, 2.5 ml of the reaction terminating solution of the terminating and color developing reagent solution was added to terminate the enzymatic reaction, and after allowing to stand at 25° C. for 10 minutes, the absorbance at 405 nm or 645 nm was measured, in which

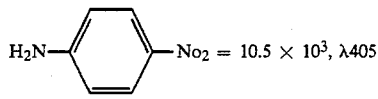 $= 10.5 \times 10^3, \lambda 405$

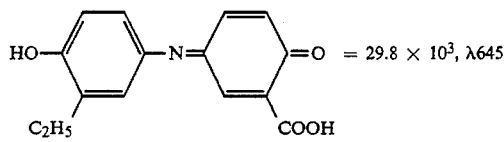 $= 29.8 \times 10^3, \lambda 645$

| | Results of Comparison of Substrate Specificity | | | | | |
|---|---|---|---|---|---|---|
| | Substrate | TH | PL | KL | FXa | UK |
| 1. S-2238 | H—D-Phe—Pip—Arg—PNA | 0.255 | 0.139 | 0.008 | 0.023 | 0.014 |
| 2. CH—TH | ToS—Gly—Pro—Arg—PNA | 0.318 | 0.489 | 0.020 | 0.641 | 0.057 |
| 3. TH—PNA | H—D-Phe—Pro—Arg—PNA | 0.274 | 0.217 | 0.007 | 0.055 | 0.019 |
| 4. NT—A | H—D-Val—Pro—Arg—CHA | 0.219 | 0.012 | 0.007 | 0.019 | 0.002 |
| 5. NT—B | H—D-Leu—Pro—Arg—CHA | 0.192 | 0.028 | 0.009 | 0.020 | 0.002 |
| 6. NT—C | H—D-Phe—Pro—Arg—CHA | 0.428 | 0.009 | 0.007 | 0.014 | 0.001 |
| 7. NT—D | H—D-Ser(OBzl)—Pro—Arg—CHA | 0.451 | 0.024 | 0.045 | 0.030 | 0.000 |
| 8. NT—E | H—D-Thr(OBzl)—Pro—Arg—CHA | 0.255 | 0.009 | 0.005 | 0.015 | 0.004 |
| 9 NT—F | H—D-Tyr(OBzl)—Pro—Arg—CHA | 0.324 | 0.052 | 0.019 | 0.011 | 0.004 |
| 10 NT—D | H—D-Lys(ToS)—Pro—Arg—CHA | 0.306 | 0.096 | 0.020 | 0.014 | 0.003 |

Initial Substrate Concentration So = 0.54 mmole/l
The measured values indicate the absorbances (O.D.), in which the wavelength used are 405 nm for Nos. 1–3 and 645 nm for Nos. 4–10.

What is claimed is:

1. A method for measuring the activity of thrombin in plasma which comprises (a) reacting a compound of the following formula or a salt thereof

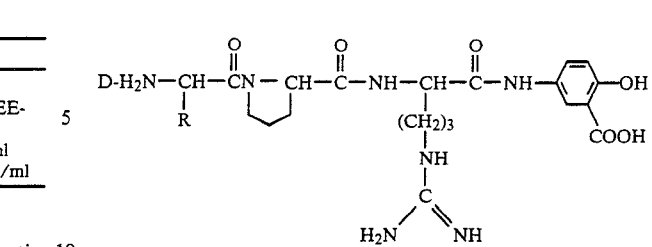

wherein R represents

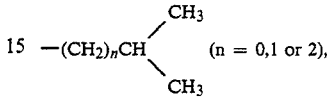 (n = 0,1 or 2),

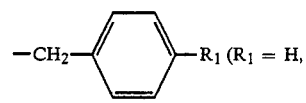 (R$_1$ = H,

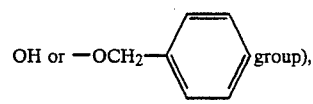 group),

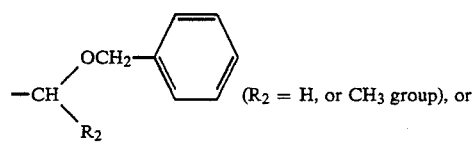 (R$_2$ = H, or CH$_3$ group), or

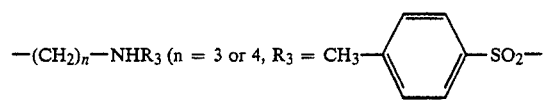

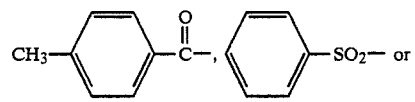

with thrombin in a buffer solution having a pH of 8.0 to 8.7 to produce 3-carboxy-4-hydroxyaniline, (b) oxidatively condensing said aniline with a coupler to form a colored compound and (c) quantitatively determining said colored compound by colorimetry or fluorometry.

* * * * *